(12) United States Patent
Murdeshwar et al.

(10) Patent No.: US 10,456,154 B2
(45) Date of Patent: Oct. 29, 2019

(54) ELECTROSURGICAL FORCEPS WITH RESILIENT JAWS

(71) Applicant: GYRUS ACMI, INC., Southborough, MA (US)

(72) Inventors: Nikhil M. Murdeshwar, Maple Grove, MN (US); John Mensch, Plymouth, MN (US); Zane R. Ward, Prior Lake, MN (US); Kester J. Batchelor, Mound, MN (US); Richard A. Thompson, II, St. Louis Park, MN (US); Evan M. Leingang, Plymouth, MN (US); Jeffrey J. Nelson, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 427 days.

(21) Appl. No.: 15/386,537

(22) Filed: Dec. 21, 2016

(65) Prior Publication Data

US 2017/0100147 A1 Apr. 13, 2017

Related U.S. Application Data

(63) Continuation of application No. 14/921,079, filed on Oct. 23, 2015, now Pat. No. 9,561,046.
(Continued)

(51) Int. Cl.
*A61B 17/295* (2006.01)
*A61B 17/29* (2006.01)
(Continued)

(52) U.S. Cl.
CPC ............ *A61B 17/295* (2013.01); *A61B 17/29* (2013.01); *A61B 18/1447* (2013.01);
(Continued)

(58) Field of Classification Search
CPC ............ A61B 17/29; A61B 2017/2926; A61B 2017/2937; A61B 2017/2947; A61B 18/1447
See application file for complete search history.

(56) References Cited

U.S. PATENT DOCUMENTS

| | | | |
|---|---|---|---|
| 2,397,823 | A | 4/1946 | Walter |
| 3,515,139 | A | 6/1970 | Mallina |

(Continued)

FOREIGN PATENT DOCUMENTS

| | | |
|---|---|---|
| DE | 3739019 A1 | 5/1989 |
| EP | 2578174 A1 | 4/2013 |
| EP | 2594211 A1 | 5/2013 |

OTHER PUBLICATIONS

US 8,419,756 B2, 04/2013, Stulen et al. (withdrawn)
(Continued)

*Primary Examiner* — Ashley L Fishback
(74) *Attorney, Agent, or Firm* — The Dobrusin Law Firm, P.C.

(57) ABSTRACT

The teachings herein provide an instrument comprising a forceps. The forceps comprise a hand piece; a tubular member connected to the hand piece; and a jaw assembly connected to the hand piece. The jaw assembly includes a first jaw element and a second jaw element. The first jaw element includes a gripping section and a flexing section. The flexing section includes an arcuate section. The second jaw element opposes the first jaw element and includes a gripping section. The tubular member is moveable onto the arcuate section of the first jaw element so that the flexing section of the first jaw element is flexed and the jaw assembly is moved into a closed position. The first jaw element, the second jaw element, or both include a stiffening spine so that the jaw assembly is substantially rigid in the closed position.

21 Claims, 6 Drawing Sheets

Related U.S. Application Data (60) Provisional application No. 62/068,101, filed on Oct. 24, 2014.

(51) Int. Cl.
*A61B 18/14* (2006.01)
*A61B 18/00* (2006.01)

(52) U.S. Cl.
CPC .......... *A61B 2017/2925* (2013.01); *A61B 2017/2926* (2013.01); *A61B 2017/2937* (2013.01); *A61B 2017/2947* (2013.01); *A61B 2018/0063* (2013.01); *A61B 2018/00077* (2013.01); *A61B 2018/00083* (2013.01); *A61B 2018/00101* (2013.01); *A61B 2018/00589* (2013.01); *A61B 2018/00601* (2013.01); *A61B 2018/00607* (2013.01); *A61B 2018/00791* (2013.01); *A61B 2018/1455* (2013.01)

(56) References Cited

U.S. PATENT DOCUMENTS

| | | |
|---|---|---|
| 3,815,609 A | 6/1974 | Chester |
| 3,934,589 A | 1/1976 | Zimmer |
| 3,967,625 A | 7/1976 | Yoon |
| 4,003,380 A | 1/1977 | Wien |
| 4,005,714 A | 2/1977 | Hiltebrandt |
| 4,016,881 A | 4/1977 | Rioux et al. |
| 4,418,692 A | 12/1983 | Guay |
| 4,427,014 A | 1/1984 | Bel et al. |
| 4,955,897 A | 9/1990 | Ship |
| 5,104,397 A | 4/1992 | Vasconcelos et al. |
| 5,250,056 A | 10/1993 | Hasson |
| 5,258,006 A | 11/1993 | Rydell et al. |
| 5,286,255 A | 2/1994 | Weber |
| 5,304,203 A | 4/1994 | El-Mallawany et al. |
| 5,312,391 A | 5/1994 | Wilk |
| 5,318,013 A | 6/1994 | Wilk |
| 5,318,589 A | 6/1994 | Lichtman |
| 5,342,359 A | 8/1994 | Rydell |
| 5,354,313 A | 10/1994 | Boebel |
| 5,445,638 A | 8/1995 | Rydell et al. |
| 5,458,598 A | 10/1995 | Feinberg et al. |
| 5,462,546 A | 10/1995 | Rydell |
| 5,474,057 A | 12/1995 | Makower et al. |
| 5,499,997 A | 3/1996 | Sharpe et al. |
| 5,499,998 A | 3/1996 | Meade |
| 5,549,627 A | 8/1996 | Kieturakis |
| 5,562,699 A | 10/1996 | Heimberger et al. |
| 5,573,535 A | 11/1996 | Viklund |
| 5,590,570 A | 1/1997 | LeMaire, III et al. |
| 5,611,813 A | 3/1997 | Lichtman |
| 5,620,459 A | 4/1997 | Lichtman |
| 5,626,595 A | 5/1997 | Sklar et al. |
| 5,667,526 A | 9/1997 | Levin |
| 5,702,390 A | 12/1997 | Austin et al. |
| 5,735,849 A | 4/1998 | Baden et al. |
| 5,849,022 A | 12/1998 | Sakashita et al. |
| 5,891,142 A | 4/1999 | Eggers et al. |
| 6,050,996 A | 4/2000 | Schmaltz et al. |
| 6,110,171 A | 8/2000 | Rydell |
| 6,113,596 A | 9/2000 | Hoovwn et al. |
| 6,146,388 A | 11/2000 | McDonald |
| 6,152,923 A | 11/2000 | Ryan |
| 6,190,386 B1 | 2/2001 | Rydell |
| 6,245,070 B1 | 6/2001 | Marquis et al. |
| 6,248,123 B1 | 6/2001 | McDonald |
| 6,270,497 B1 | 8/2001 | Sekino et al. |
| 6,293,954 B1 | 9/2001 | Fogarty et al. |
| 6,458,130 B1 | 10/2002 | Frazier et al. |
| 6,464,702 B2 | 10/2002 | Schulze et al. |
| 6,506,209 B2 | 1/2003 | Ouchi |
| 6,524,309 B1 | 2/2003 | Watrelot et al. |
| 6,585,735 B1 | 7/2003 | Frazier et al. |
| 6,679,882 B1 | 1/2004 | Kornerup |
| 6,802,843 B2 | 10/2004 | Truckai et al. |
| 6,916,054 B1 | 7/2005 | Baldesberger |
| 6,929,645 B2 | 8/2005 | Battles et al. |
| 6,989,017 B2 | 1/2006 | Howell et al. |
| 7,101,371 B2 | 9/2006 | Dycus et al. |
| 7,108,694 B2 | 9/2006 | Miura et al. |
| 7,115,139 B2 | 10/2006 | McClurken et al. |
| 7,150,749 B2 | 12/2006 | Dycus et al. |
| 7,232,440 B2 | 6/2007 | Dumbauld et al. |
| 7,473,253 B2 | 1/2009 | Dycus et al. |
| 7,632,269 B2 | 12/2009 | Truckai et al. |
| 7,699,835 B2 | 4/2010 | Lee et al. |
| 7,749,222 B2 | 7/2010 | Lu et al. |
| 7,766,910 B2 | 8/2010 | Hixson et al. |
| 7,837,631 B2 | 11/2010 | Diamond et al. |
| 8,137,263 B2 | 3/2012 | Marescaux et al. |
| 8,262,655 B2 | 9/2012 | Ghabrial et al. |
| 8,328,802 B2 | 12/2012 | Deville et al. |
| 8,409,197 B2 | 4/2013 | Slater |
| 8,425,511 B2 | 4/2013 | Olson |
| 8,460,275 B2 | 6/2013 | Taylor et al. |
| 8,496,674 B2 | 7/2013 | Cabrera et al. |
| 8,523,898 B2 | 9/2013 | Bucciaglia et al. |
| 8,535,312 B2 | 9/2013 | Horner |
| 8,641,712 B2 | 2/2014 | Couture |
| 8,715,277 B2 | 5/2014 | Weizman |
| 2003/0229344 A1 | 12/2003 | Dycus et al. |
| 2005/0049633 A1 | 3/2005 | Waranabe |
| 2006/0052777 A1 | 3/2006 | Dumbauld |
| 2006/0084973 A1 | 4/2006 | Hushka |
| 2006/0190035 A1 | 8/2006 | Hushka et al. |
| 2006/0208506 A1 | 9/2006 | Kern et al. |
| 2007/0123855 A1 | 5/2007 | Morley et al. |
| 2008/0119870 A1 | 5/2008 | Williams |
| 2009/0062792 A1 | 3/2009 | Vakharia et al. |
| 2010/0179540 A1 | 7/2010 | Marczyk et al. |
| 2011/0054462 A1 | 3/2011 | Ellman |
| 2011/0082494 A1 | 4/2011 | Kerr et al. |
| 2012/0022530 A1 | 1/2012 | Woodruff et al. |
| 2012/0074200 A1 | 3/2012 | Schmid et al. |
| 2012/0191091 A1 | 7/2012 | Allen |
| 2012/0253344 A1 | 10/2012 | Dumbauld et al. |
| 2013/0014375 A1 | 1/2013 | Hempstead et al. |
| 2013/0085516 A1 | 4/2013 | Kerr et al. |
| 2013/0131651 A1 | 5/2013 | Strobl et al. |

OTHER PUBLICATIONS

A New Tool for Minor-Access Surgery, IEEE Engineering in Medicine and Biology Magazine, vol. 17, No. 3, May 1, 1998 (May 1, 1998), pp. 45-48, XP000751405, Matthias Balazs M. et al.

International Search Report and Written Opinion for International Application No. PCT/US2015/057054, dated Feb. 5, 2016.

ELECTROSURGICAL FORCEPS WITH RESILIENT JAWS

FIELD

The present disclosure relates to an instrument, and more particularly to a forceps instrument having resilient or flexible jaws.

BACKGROUND

Generally, forceps are plier-like instruments that have opposing jaws. The forceps can be used during a medical procedure to effect an anatomical feature of interest such as a vessel or tissue. For example, some forceps can be used to move, grip, grasp, push, pull, cut, coagulate, dissect and or otherwise effect a vessel or tissue. The forceps can also be used in non-medically related procedures to move, grip, grasp, push, pull, cut, and or otherwise effect an object. Some forceps also include electrosurgical capabilities for cutting and/or coagulating an anatomical feature.

Forceps typically include jaws that are moveable between an open and closed position. Some forceps have rigid or inflexible jaws so that a uniform gripping and/or grasping force can be applied to an object or anatomical feature between the jaws. However, unless the forceps include a discontinuous joint, mechanism and or assembly, rigid or inflexible jaws may be difficult to move between the open and closed position. A discontinuous joint, mechanism, and or assembly may, however, require multiple parts to be assembled onto the forceps, which may undesirably add time and cost to the manufacturing and or assembly process. Moreover, a discontinuous joint, mechanism, and or assembly may increase a section size of the forceps, which may restrict use of the forceps in laparoscopic procedures, for example.

Instead of rigid or inflexible, jaws having discontinuous joints, mechanisms, and or assemblies, some forceps have resilient or flexible jaws. That is, the resilient or flexible jaws can be moved or biased between an open and closed position without a discontinuous joint, mechanism, and/or assembly. However, due to jaw deflection, some challenges exist in providing a uniform gripping and or grasping forces between the jaws with such resilient or flexible jaws. Some examples of forceps are taught in U.S. Pat. Nos. 5,735,849 and 5,445,638, the disclosures of Which are hereby incorporated by reference herein in their entireties for all purposes.

It may therefore be desirable to improve the current state in the art by proving an instrument or forceps having one or more resilient or flexible jaws capable of providing a uniform gripping and/or grasping forces between the jaws without a discontinuous joint, mechanism, and/or assembly. That is, it may be desirable to provide jaws that are capable of applying a uniform gripping and/or grasping force to an object or anatomical feature provided between the gripping portions or a jaw assembly.

SUMMARY

The teachings included herein provide an instrument. The instrument may be a medical instrument such as a medical forceps including one or flexible and/or resilient jaw elements. The instrument may also be a non-medically related instrument or forceps including one or more flexible and/or resilient jaw elements. A stiffening spine, jaw shroud, or both is provided on one or both of the jaw elements, which may function to stiffen or reinforce the gripping section or portions of the jaw assembly. Accordingly, the jaw elements can be moved or biased into a closed or gripping position, without requiring a discontinuous joint, while providing a substantially uniform gripping and/or grasping forces to an object or anatomical feature located between the jaws, the griping portions, or both.

The teachings herein desirably provide a forceps instrument that can be manufactured relatively inexpensively and quickly due to not having or requiring complicated and/or costly discontinuous joints, mechanisms, and/or assemblies. The teachings herein provide an instrument or forceps that can be used in various non-medical and medical procedures, such as open and laparoscopic or minimally invasive procedures.

The teachings herein provide an instrument comprising a forceps. The forceps comprise a hand piece; a tubular member connected to the hand piece; and a jaw assembly connected to the hand piece. The jaw assembly includes a first jaw element and a second jaw element. The first jaw element includes a gripping section and a flexing section. The flexing section includes an arcuate section. The second jaw element opposes the first jaw element and includes a gripping section. The tubular member is moveable onto the arcuate section of the first jaw element so that the flexing section of the first jaw element is flexed and the jaw assembly is moved into a closed position. The first jaw element, the second jaw element, or both includes a stiffening spine so that the jaw assembly is substantially rigid in the closed position.

The teachings also provide an instrument comprising a forceps, which comprise a hand piece; a tubular member moveably connected to the hand piece; and a jaw assembly connected to the hand piece. The jaw assembly includes a first jaw element comprising a gripping portion and an arcuate section; and a second jaw element comprising a gripping portion. The tubular member is moveable over the arcuate section of the first jaw element so that the first jaw element is flexed and the jaw assembly is moved into a closed position. The first jaw element includes a jaw shroud so that a uniform gripping pressure is provided along the gripping portion of the first jaw element and the gripping portion of the second jaw element.

The teachings further provide an instrument comprising a forceps. The forceps include a hand piece, a tubular member moveably connected to the hand piece; and a jaw assembly connected to the hand piece. The jaw assembly comprises a first jaw element, a second jaw element, a stabilizing spine, and a jaw shroud. The first jaw element comprises a gripping portion and an arcuate section. The second jaw element comprises a gripping portion and an arcuate section. The stabilizing spine is connected to one or both of the first jaw element and the second jaw element. The jaw shroud is connected to the stabilizing spine. The tubular member is moveable over the arcuate section of the first jaw element and the arcuate section of the second jaw element so that both the first jaw element and the second jaw element are flexed and the jaw assembly is moved, into a closed position. The stabilizing spine and the jaw shroud function to restrict the gripping portion of the first jaw element, the gripping portion of the second jaw element, or both from deflecting when the jaw assembly is in the closed position so that a uniform gripping pressure is provided along the gripping portion of the first jaw element and the gripping portion of the second jaw element.

DETAILED DESCRIPTION

This disclosure claims the benefit of U.S. Provisional Patent Application No. 62/068,101 filed on Oct. 24, 2014, the disclosure of which is hereby incorporated by reference herein in its entirety for all purposes.

The explanations and illustrations presented herein are intended to acquaint others skilled in the an with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the hill scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide one or more instruments. The instrument can be any suitable instrument used to manipulate, engage, move, grasp, grip, push, pull, cut, tear, coagulate, seal, cauterize, dissect, fulgurate, or otherwise effect an anatomical feature of interest, such as a vessel, tissue, vein, artery, the like, or a combination thereof. The instrument can be used in open and/or in laparoscopic or minimally invasive procedures. The instrument can be a medical forceps, a cutting forceps, or both. The instrument according to the teachings herein can be used in various non-medically related procedures. That is the instrument can be used to effectively manipulate, engage, move, grasp, grip, push, pull, cut, tear, seal, cauterize, or otherwise effect an object of interest that is not an non-anatomical feature.

The instrument may be used with or without power. When used with power, the instrument can be used in electrosurgery. The instrument can be used in a monopolar circuit, a bipolar circuit, or both. The instrument may be used with monopolar energy, bipolar energy, blended energy, or a combination thereof. For example, a suitable current, therapy, and/or signal may be passed from, through, or between one or more of the jaws, a remote pad, a patient or anatomy, or a combination thereof so that an object or anatomical feature can be cut, coagulated, or both.

The instrument may include a hand piece. The hand piece may function to house, support, and/or contain one or more working functions or assemblies of the instrument; the parts of components needed to move or actuate the one or more working functions or assemblies; or a combination thereof. The one or more working functions or assemblies may include a gripping function for gripping, pulling, constricting, coagulating, and/or sealing an object or anatomical feature; a cutting function for cutting, transecting, dissecting an object or anatomical feature; or both. The instrument, the hand piece, or both may include sufficient controls for operating, actuating, and/or manipulating the one or more working functions or assemblies. The controls may be located anywhere on instrument, the hand piece, at a remote location, or a combination thereof.

The tubular member may function to permit a portion of the instrument to be inserted into a patient or the anatomy, while a portion of the instrument remains outside of the patient or anatomy. The tubular member may be moveable so that the jaw assembly can be moved between an open and closed position. The tubular member may be configured to be inserted into the anatomy through a trocar. The tubular member may allow for the jaw assembly and/or one or more functional elements to be manipulated without being impeded by a trocar, the anatomy, or both.

The tubular member may be an elongated member that extends along an axis (i.e., a tubular member axis) between opposing proximal and distal ends. The proximal end of the tubular member may be suitably and sufficiently connected to the hand piece. The distal end may define an opening (i.e., a distal opening). The tubular member may be at least partially hollow and may define therein an inner portion. The hollow or inner portion of the tubular member, the distal opening, or both, may be sufficiently sized so that the tubular member can be moved (i.e., axially, distally, proximally, or a combination thereof) relative to the flexing sections and/or the arcuate sections of one or more of the jaw elements, the hand piece, or a combination thereof. The tubular member may be substantially straight; may include one or more angles, bends or arcs; or a combination thereof. The tubular member may be substantially rigid, substantially flexible, substantially resilient, or a combination thereof.

The tubular member may be movable relative to the jaw assembly, the hand piece, or both so that the jaw assembly can be moved or flexed between an open position and a closed position. More specifically, by manipulating one or more user inputs, the tubular member can be moved in a first direction (i.e., distally relative to the hand piece) over and/or onto the flexing section, the arcuate portion, or both of one or more of the jaw elements so that the jaw assembly can be moved into a closed or gripping position. The closed position may be defined as a position of the jaw elements where virtually no gap or only a slight gap exists between the gripping portions, the electrically conductive portions or both of the jaw elements. Additionally or alternatively, in the closed position, a clamping, or gripping force of the gripping portions, the electrically conductive portions or both of the jaw elements may be higher or larger than a clamping or gripping force between the gripping portions, the electrically conductive portions, or both of the jaw elements when the jaws are in the open position.

The tubular member can be moved in an opposing, second direction (e.g., proximally relative to the hand piece) so that the jaw assembly can be moved into the open position. The open position may be defined as the jaw elements being in a spaced apart relationship relative to one another. That is, in the open position, a gap may extend between gripping portions, the electrically conductive portions, or both of the jaw elements. Additionally or alternatively, in the open position, the clamping or gripping, force between the gripping portions, the electrically conductive portions, or both of the jaw elements may be less than the clamping or gripping force between the gripping portions, the electrically conductive portions, or both of the jaw elements when the jaw assembly is in the closed position.

The instrument may include one or more jaw assemblies. The jaw assembly may be configured to perform one or more device functions. For example, the one or more device functions may include effecting an object or anatomical feature of interest, such as: capturing an object or vessel or tissue; grasping an object or vessel or tissue; providing a clamping force to secure an object, vessel or tissue; providing retraction of an object, vessel or tissue; providing a compression force across an object, vessel or tissue captured in the jaw assembly; or a combination thereof. The jaw assembly may be used in electrosurgery to cut, coagulate, cauterize, dissect, and/or fulgurate an anatomical feature. The jaw assembly can be moved or flexed between an open and closed position. Preferably, the jaw assembly does not include any discontinuous mechanisms, joints, and/or assemblies to move the jaw assembly between the open and closed positions.

The jaw assembly may include one or more jaw elements. The jaw elements may be moved or articulated to perform one or more of the aforementioned device functions. The jaw elements may be moved or articulated when the jaw assembly is moved between the open and closed positions. The jaw elements may be arranged to oppose one another. The jaw elements may include an upper jaw element and an identical lower jaw element. Alternatively, the jaw elements need not be identical; that is, the geometry of the upper jaw element may be different from the lower jaw element. For example, one of the jaw elements may include a flexing section having one or more arcuate portions or sections, and another one of the jaw elements may be free of a flexing section, one or more arcuate portions or sections. The jaw elements may be substantially rigid; substantially flexible; substantially resilient, or a combination thereof. That is, the jaw elements may have one or more sections that are substantially rigid; one or more sections that are substantially flexible; one or more sections that are substantially resilient, or a combination thereof. The one or more jaw elements may include a flexing section, an anchoring section, and a gripping section.

The one or more jaw elements may be fabricated from any suitable material. Preferably, the jaw elements are fabricated from a material that is suitable for use in medical procedures, and is flexible, yet strong. For example, the jaw elements may be made from sheet metal or wire. Preferably, the jaw elements are fabricated from as material that can pass current so that one or more of the jaw elements or jaws can be used in electrosurgery. One or more of the jaw elements may be in communication with a generator or a source of one or more electrosurgical therapies or currents for use in electrosurgical procedures. One or more sections of the jaw elements may be covered or coated in an insulating material so that electrical shorts can be prevented if the jaw elements come into contact.

In a neutral or a steady state position, the jaw assembly may be in either an open position or in a closed position. Preferably, in a neutral or steady state position, the jaw assembly is in the open position. By manipulating or actuating one or more user inputs or mechanisms, the jaw assembly, the jaw elements, or both can be moved or flexed into a closed position. More specifically, the tubular member can be moved distally relative to the hand piece over and/or onto one or more of the arcuate sections of one or more of the jaw elements, which may therefore cause one or both of the jaws or jaw elements to move, pivot, and/or flex into the closed position. That is, the upper jaw element, the gripping portion of the upper jaw element, or both may move or flex towards the lower jaw element and/or the gripping portion of the upper jaw element, or vice versa. Alternatively, the upper jaw element or a gripping portion thereof may be moved or flexed towards the lower jaw element, and the lower jaw element or a gripping portion thereof may be moved or flexed towards the upper jaw element or gripping portion thereof.

By manipulating or actuating one or more user inputs, the tubular member can be moved proximally relative to the hand piece and off of the arcuate sections of one or both of the jaw elements, which may therefore cause one or both of the jaws or jaw elements to move, pivot, flex and/or relax into the open position. That is, the upper jaw element, the gripping portion of the upper jaw element, or both may move or flex away from the lower jaw element and/or the gripping portion of the upper jaw element, or vice versa. Alternatively, the upper jaw element or a gripping portion thereof may be moved or flexed away from the lower jaw element, and the lower jaw element or a gripping portion thereof may be moved or flexed away from the upper jaw element or gripping portion thereof.

It may be preferred that the jaw assembly, the jaw elements, or both may be restricted from translating or moving axially relative to the hand piece. In some configurations, however, one or both of the jaw elements may be moveable relative to the hand piece. That is, the proximal ends or portions of the flexing sections, the arcuate sections, or both of one or more of the jaw elements may be restricted or prevented from moving relative to the hand piece.

The jaw assembly, one or more of the jaw elements, or both can be rotated while the jaw assembly is in an open position, closed position, or in a position there between. Rotating the jaw assembly, one or more of the jaw elements, or both may provide for a user to alter an orientation or approach of the jaw assembly relative to an object, vessel or tissue without having to twist or adjust the hand piece into a difficult or uncomfortable position. To rotate the jaw assembly, one or more of the jaw elements, or both a user can manipulate or actuate one or more user inputs or mechanism, such as turning or rotating a rotation wheel on the hand piece, which in turn causes a rotation mechanism to rotate the jaw assembly, the jaw elements, or both.

The one or more jaw elements may include one or more flexing sections. The one or more flexing sections may cooperate with the tubular member and function to move the jaw assembly, the one or more jaw elements, or both between an open and closed position. The flexing sections may be at least partially flexible and/or resilient so that the flexing sections, the jaw assembly, the one or more jaw elements, or both can be moved, bent, pivoted, or the like when a pressure or force is applied thereto. When the pressure or force is released or removed, the flexing sections, the jaw assembly, the one or more jaw elements, or a combination thereof can move, bend, or relax back to an initial, steady state position. At least the proximal ends or portions of the flexible sections may be restricted or prevented from moving relative to the hand piece especially when the jaw assembly is moved between the open and closed positions.

The flexing sections may include one or more raised or arcuate sections. When a pressure or force is applied to the one or more raised or arcuate sections, the jaw assembly, a corresponding jaw element, or both may can move, bend, or flex into a closed position. The jaw assembly, the one or more jaw elements, or a combination thereof can move, bend, or relax back to an initial, steady state position once the pressure or force is released or minimized or otherwise removed from the arcuate or raised portions. At least the proximal ends or portions of the arcuate sections may be restricted or prevented from moving relative to the and piece especially when the jaw assembly is moved between the open and closed positions. The one or more raised or arcuate sections can be any feature that is at least partially taller, wider, and/or larger than the tubular member, an inner portion of the tubular member, an opening of the tubular member (e.g., the distal opening), or a combination thereof. For example, the one or more raised or arcuate sections can be a thickened portion of the jaw elements or a projection attached to one or both of the jaw elements.

The one or more jaw elements may include one or more anchoring sections. The one or more anchoring sections may function to anchor or connect the jaw elements, the jaw assembly, or both to the hand piece. The anchoring sections may be connected to one or more anchoring rods. The anchoring section may be integrally formed with the anchoring rod, or may be connected thereto via any suitable method, such as welding, soldering, adhesives, stamping, etc. The anchoring rods may be connected to one or more mechanisms in the hand piece, so that when a user actuates one or more user controls, the mechanisms, the anchoring rods, and therefore the jaw elements and/or jaw assembly is moved. The anchoring rods may be connected to one or more electrodes. The anchoring rods may be electrically conductive. The anchoring rods may be in electrical communication with the generator. For example, at their distal ends, the anchoring rods may be connected to corresponding electrodes, and at their proximal ends the anchoring rods may be in communication with the generator, one or more electrical leads, wires, or a combination thereof. Preferably, the anchoring rods may be insulated from one another so that a short between the anchoring rods is prevented.

The anchoring sections may include one or more extensions that extend from the flexing sections, the gripping sections, or both. Preferably, each anchoring section includes two extensions. One or more webs may laterally connect the extensions so that the anchoring section is generally rigid. Preferably, the anchoring section has a small profile or section so that the anchoring section can fit inside an inner portion of the tubular member and can easily slide within the tubular member when the tubular member is moved distally, proximally, or both. The anchoring section can be made from a thin or thinner gage of material (i.e., wire or sheet metal) compared to the other sections of the jaw elements (i.e., the gripping section, the flexing section, or both). The anchoring section can include one or more recesses. The one or more recesses may function to increase the area in contact with the anchor rod for welding or soldering the anchoring section to a corresponding anchoring rod.

The one or more jaw elements may include one or more gripping sections. The one or more gripping sections may function to manipulate, capture, engage, move, grasp, grip push, pull, cut, tear, coagulate, seal, cauterize, dissect, fulgurate, or otherwise elect an object or anatomical feature of interest, such as a vessel, tissue, vein, artery, the like, or a combination thereof. The one or more gripping sections may be located at or near a distal end, section, or portion of one or more of the jaw elements. The one or more gripping sections may include one or more jaws, one or more stiffening spines, and/or one or more jaw shrouds.

The one or more jaws may function to manipulate, capture, engage, move, grasp, grip push, pull, cut, tear, coagulate, seal, cauterize, dissect, fulgurate, or otherwise effect or perform a device function on an object or anatomical feature of interest, such as a vessel, tissue, vein, artery, the like, or a combination thereof. Preferably, uniform gripping and/or grasping forces can be provided along a length of the jaws or along, as length of the gripping portions of each jaw when the jaw assembly is in the closed position, is being moved into the closed position, and/or is being moved from the closed position to the open position.

The one or more jaws may include one or more gripping portions. The one or more gripping portions may function to manipulate, capture, engage, move, grasp, grip push, pull, cut, tear, coagulate, seal, cauterize, dissect, fulgurate, or otherwise effect or perform a device function on an object or an anatomical feature of interest, such as a vessel, tissue, vein, artery, the like, or a combination thereof a non-anatomical feature or object of interest, or a combination thereof. The gripping portion may be located in an area or region between a distal tip or end of a jaw or jaw element and a distal portion or area of the arcuate section or flexing section.

The one or more gripping portions may be electrically conductive. That is, the gripping portions may include one or more electrically conductive portions. The one or more gripping portions, electrically conductive portions, or both may function to pass one or more therapy signals or currents between the gripping portions, electrically conductive portions, an object, the anatomy, or a combination thereof. The one or more griping portions, electrically conductive portions, or both may be an electrode or may be in communication with an electrode or otherwise in communication with a generator. The one or more electrically conductive portions may be an entire portion of the gripping portions. That is, the one or more electrically conductive portions may extend in an area or region between a distal tip of one or more of the jaws or jaw elements and a distal portion of the arcuate sections or flexing sections. The one or more electrically conductive portions may comprise a smaller area or portion of the gripping portions. In other words, the one or more electrically conductive portions may take up a smaller area or portion between the distal tip of the jaw or jaw assembly and a distal portion of the arcuate or flexing sections. A proximal end or portion of the one or more electrically conductive portions may be aligned with or the same as to proximal end or portion of the one or more gripping portions.

The one or more gripping portions may also include one or more insulated portions or non-electrically conductive portions. The one or more insulated or non-electrically conductive portions may be insulated or otherwise not connected to an electrode or generator. Accordingly, the one or more non-electrically conductive portions may be unable or restricted from passing a therapy current between the jaws, an object, the anatomy, or a combination thereof.

The one or more jaws, gripping portions, electrically conductive portions, non electrically conductive portions, or a combination thereof may include one or more areas having teeth, no teeth, projections, or a combination thereof. The one or more teeth or projections may be formed or cut into the jaw or gripping portion by a suitable process or method, such as by grinding, electrical discharge machining, stamping, coining, etc. The one or more jaws or gripping portions may include one or more troughs between the teeth to separate one tooth from another. The one or more teeth may have sharp points to assist in grasping an object or tissue. Alternatively, or in addition, the one or more teeth may have flattened tops to distribute forces associated with grasping forces so that the object or tissue, especially vessel walls, are not punctured or otherwise damaged when an object, vessel, or tissue is between the jaws in the closed position. Puncturing an object or tissue may undesirably cause the two opposing jaws or gripping portions to contact one another, which may cause an electrical short if the one or both of the jaws are electrically charged. The one or more gripping portions may include one or more projections that may be the same as or different from the projections described herein on the jaw shroud, the stiffening spine, or both.

The one or move gripping portions, electrically conductive portions, jaws, or a combination thereof may include one or more electrodes. The one or more electrodes may be used in electrosurgery. The one or more electrodes may function to cauterize, dissect, cut and/or coagulate an object, vessel or tissue between the jaws, gripping portion, or both. The one or more electrodes may be in a monopolar electrosurgical circuit, as bipolar electrosurgical circuit, to blended circuit, or a combination thereof. The one or more electrodes may be in communication with a generator or other source of electrosurgical current. The one or more electrodes may be in communication with the one or more gripping portions, the one or more electrically conductive portions, or both so that a suitable therapy current can be passed between the electrodes, through an object or feature of the anatomy, to a remote patient pad, or a combination thereof. The one or more electrodes may be in communication with the jaw anchoring rods, one or more wires, traces, or both, which may be in electrical communication with the generator. To excite the bipolar energy, a user can depress or otherwise actuate one or more user input controls, such as a button on the hand piece or a foot pedal at a remote location, for example, which may close an electrical switch so that electrical energy can communicate between the generator to the one or more electrodes, electrically conductive portions, or both. The one or more electrodes may also function to pass monopolar energy between one or more of the electrodes and a remote patient pad.

The one or more jaw shrouds may function to reinforce or stiffen the gripping section, the jaws, the jaw elements, the gripping portions, the electrically conductive portions, or a combination thereof. The jaw shroud may function to provide the jaw assembly with a substantially uniform grasping or gripping pressure or force in the gripping portion, electrically conductive portion or both. The jaw shroud may function to overcome beam deflection in one or both of the jaws, gripping portions, electrically conductive portions, or a combination thereof when the jaw assembly is in a closed position or is being moved into the closed position especially when an object, vessel, or tissue is located between the jaws. The jaw shroud may function to stiffen the gripping section or gripping portion without the need for one or more stiffening spines.

The jaw shroud may be fabricated from a suitable material. Preferably, the jaw shroud is fabricated from a material that is suitable for use in medical procedures, such as metal and/or plastic, for example. The jaw shroud may be formed by any suitable process, such as stamping, metal injection molding (MIM), or plastic injection molding, for example. The jaw shroud may be thermally insulating so that a thermal barrier can be provided between the jaws, the jaw assembly, or both. A thermally insulting shroud may be preferred in some applications so that thermal spread is limited or reduced. The jaw shroud may be electrically insulating to prevent, an electrical short when the instrument is used in electrosurgery.

A jaw shroud may be attached to one or both of the jaws or jaw elements. That is, a jaw shroud can be attached to an upper jaw or jaw element, a lower jaw or jaw element, or both jaws and jaw elements. The jaw shroud may be attached to the one or more jaws, jaw elements, or both in any suitable manner. For example, the jaw shroud may be bonded or over-molded onto a jaw element, jaw, stiffening spine, or a combination thereof. For example, the jaw shroud can be slipped-on or slipped-over a distal end of a stiffening spine, a jaw element, a jaw, or a combination thereof. For example, the jaw shroud may be attached, connected, interlaced, welded, ultrasonically welded, staked, adhered, or a combination thereof onto the stiffening spine, a jaw element, jaw, or a combination thereof. For example, the jaw shroud can be snapped into or onto a channel, groove, or projection in or on a corresponding jaw, jaw element, and/or stiffening spine. The jaw shroud can include one or more connecting features that may cooperate with one or more undercut features on the stiffening spine, jaw, or both to attach the jaw shroud to the stiffening spine. The one or more connecting features, undercut features, or both can be welded or melted together to prevent or restrict removal or separation of the jaw shroud and the stiffening spine. The one or more connecting features, undercut feature, or both may be one or more metal or plastic mating projections, grooves, nubs, posts; mating male and female dovetail sections, or other like features suitable for connecting the spine and the shroud.

In some configurations, the jaw shroud may be irreversibly attached to the stiffening spine, jaw element, jaw, or a combination thereof. Irreversibly attached may mean that the jaw shroud cannot be separated from the stiffening spine, jaw element, jaw, or a combination thereof without substantially damaging the jaw shroud, the stiffening spine, a jaw element, jaw, or a combination thereof in some configurations, the jaw shroud may be reversibly connected to the stiffening spine, jaw element, jaw, or as combination thereof. Reversibly connected may mean that that the jaw shroud can be separated from the stiffening spine, a jaw element, jaw, or a combination thereof without substantially damaging the jaw shroud, the stiffening spine, as jaw element, jaw, or a combination thereof. In some configurations, the jaw shroud may be integrally formed with the jaw, the jaw element, stiffening spine, or a combination thereof.

The jaw shroud may be include one or more projections. The one or more projections ma function to restrict or prevent the two opposing jaws, gripping portions, electrically conductive portions and/or electrodes from contacting one another, which may undesirably cause an electrical short if the one or both of the jaws are electrically charged; may undesirably puncture or otherwise damage an object, vessel or tissue between the jaws; or both. An electrical short may be interpreted, as an error by one or more generators, which may trigger corrective electrical moves in the generator, for example. One or both of the jaw shrouds may include one or more projections. That is, the projections may be located on an upper jaw shroud, on as lower jaw shroud, or located on both jaw shrouds. The one or more projections may be of substantially equal height, or the height of the projections may vary. Preferably, the one or more projections are shorter than the one or more stabilizing tongues described below. The one or more projections may be fabricated from the same material as the rest of the jaw shroud, or may be fabricated from different materials. For example, the jaw shroud can be fabricated from plastic or metal, while the one or more projections can be fabricated from metal or plastic, respectively.

The one or more stiffening spines may function to reinforce or stiffen the gripping section, the jaws, the jaw elements, the gripping portions, the electrically conductive portions, or a combination thereof. The stiffening spines may function to provide the jaw assembly with a substantially uniform grasping or gripping pressure or force in the gripping portion, electrically conductive portion or both. The stiffening spines may function to make one or both of the jaws or gripping portions substantially rigid. The stiffening spines may function to make one or both of gripping portions more rigid (i.e. less flexible) than the one or more actuate sections, the one or more flexing sections, or both. The stiffening spines may function to overcome beam deflection in one or both of the jaws, gripping portions, electrically conductive portions, or a combination thereof when the jaw assembly is in a closed position or is being moved into the closed position especially when an object, vessel, or tissue is located between the jaws. The stiffening spine may function to stiffen the gripping section or gripping portion without the need for one or more jaw shrouds.

The stiffening spine may be fabricated from a suitable material. Preferably, the stiffening spine is fabricated, from a material that is suitable for use in medical procedures, such as metal and/or plastic, for example. The stiffening spine may be formed by any suitable process, such as stamping, metal injection molding (MIM), or plastic injection molding, for example. The stiffening, spine may be thermally insulating so that a thermal barrier can be provided between the jaws, the jaw assembly, or both. A thermally insulting stiffening spine may be preferred in some applications so that thermal spread is limited or reduced. The stiffening spine may be electrically insulating to prevent an electrical short when the instrument is used in electrosurgery.

A stiffening spine may be attached to one or both of the jaws or jaw elements. That is, a stiffening spine can be attached to an upper jaw or jaw element, a lower jaw or jaw element, or both jaws and jaw elements. The stiffening spine may be attached to the one or more jaws, jaw elements, or both in any suitable manner. For example, the stiffening spine may be bonded or over-molded onto a jaw element, jaw, jaw shroud, or a combination thereof. For example, the stiffening spine can be slipped-on or slipped-over a distal end of a jaw element, a jaw, or a combination thereof. For example, the stiffening spine may be attached, connected, interlaced, welded, ultrasonically welded, staked, adhered, or a combination thereof to the jaw shroud, a jaw element, jaw, or a combination thereof. For example, the stiffening spine can be snapped into or onto a channel, groove, or projection in or on a corresponding jaw, jaw element, and/or stiffening spine. The stiffening spine can include one or more undercut features that may cooperate with one or more connecting features on the stiffening spine, jaw, or both to attach the jaw shroud to the stiffening spine. The one or more connecting features, undercut features, or both can be welded or melted together to attach and prevent or restrict separation and/or removal of the jaw shroud and the stiffening spine. The one ort more connecting features, undercut feature, or both may be one or more metal or plastic mating projections, grooves, nubs, posts, or other like features suitable for connecting the spine and the shroud.

In some configurations, the stiffening spine may be irreversibly attached to the jaw shroud, a jaw element jaw, or a combination thereof. Irreversibly attached may mean that the stiffening spine cannot be separated from the jaw shroud, jaw element, jaw, or a combination thereof without substantially damaging the jaw shroud, the jaw shroud, a jaw element, jaw, or a combination thereof. In some configurations, the stiffening spine may be reversibly connected to the jaw shroud a jaw element, jaw, or a combination thereof. Reversibly connected may mean that that the stiffening spine can be separated from the jaw shroud, a jaw element, jaw, or a combination thereof without substantially damaging the stiffening spin, the jaw shroud, a element, jaw, or a combination thereof. In some configurations, the stiffening spine may be integrally formed with the jaw, the jaw element, jaw shroud, or a combination thereof.

In some configurations, the one or more stiffening spines may extend or project from an outer or upper surface of one or both of the jaws. The outer or upper surface may oppose the gripping portion of the jaws. In some configurations, when the jaw assembly is in the open position, a gap may extend between an edge of the stiffening spine and a corresponding, jaw element, arcuate section, or both. When the jaw assembly is moved into the closed position, the edge of one or more of the stiffening spines may contact a portion of the respective jaw element, arcuate section, or froth so that the gripping portions, the jaws, or both are prevented from deflecting, especially when an object, vessel, or tissue is located between the jaws, is, one or more of the gripping sections or portions may at least partially bend, move, or flex as the jaw assembly is moved into a closed position. In the process of moving the jaw assembly into the closed position, an edge of the stiffening spine may contact a corresponding arcuate section so that the griping portion becomes less flexible or the rigidity thereof increased. Accordingly, additional moving, flexing, bending, or deflection of the gripping portion is reduced, prevented or restricted. In this regard, the jaw assembly, the gripping portions, or both can have variable flexibility as the jaw assembly is moved from the open position to the closed position; that is, the gripping portions can gave greater flexibility and less rigidity in the open position and less flexibility and more rigidity in the closed position. A uniform gripping and/or grasping pressure can provided along a length of the gripping portion of the first jaw element and the gripping portion of the second jaw element when the edge of the stiffening spine contacts or engages the corresponding jaw element, arcuate section, or both.

The stiffening spine may be include one or more projections. The one or more projections may function to restrict or prevent the two opposing jaws, gripping portions, electrically conductive portions, and/or electrodes from contacting one another, which may undesirably cause an electrical short if the one or both of the jaws are electrically charged; may undesirably puncture or otherwise damage a vessel or tissue between the jaws; or both. An electrical short may be interpreted as an error by one or more generators, which may trigger corrective electrical moves in the generator, for example. On or both of the stiffening spines may include one or more projections. That is, the projections may be located on an upper stiffening spine, on a lower stiffening spine, or located on both stiffening spines. The one or more projections may be of substantially equal height, or the height of the projections may vary. Preferably, the one or more projections are shorter than the one or more stabilizing tongues described below. The one or more projections may be fabricated from the same material as the rest of the stiffening spine, or may be fabricated from different materials. For example, the stiffening spine can be fabricated from plastic or metal, while the one or more projections can be fabricated from metal or plastic, respectively.

The one or more jaw shrouds, stiffening spines, jaws, jaw elements, or a combination thereof may include one or more stabilizing tongues. The one or more stabilizing tongues may function to provide lateral stability to the jaw assembly when the jaw assembly is in a closed position, open position, or both. The one or more stabilizing tongues may function to provide lateral stability to the jaw assembly as the jaw assembly is being moved into the open position, the closed position, or both.

The one or more stabilizing tongues may function to restrict or prevent from an object or anatomical feature from being grasped, grabbed, or otherwise positioned in the jaw assembly too far in a proximal direction towards the hand piece. In other words, the one or more stabilizing tongues may function to restrict or prevent an object or anatomical feature from being grasped, grabbed, or otherwise positioned proximally past the one or more gripping portions, electrically conductive portions, or both. For example, if an object or anatomical feature is griped, grasped or positioned in the jaw assembly too far in the proximal direction or proximally past the gripping portions or the electrically conductive portions, the object, vessel or tissue may be positioned off of the teeth, which may cause the object or anatomical feature to slip between the jaws. Additionally or alternatively, an object, vessel or tissue griped, grasped or positioned too far in a proximal direction beyond a proximal end of the gripping portion, the electrically conductive portions, or both may not be subjected to a uniform gripping or grasping forces. During electrosurgery, for example, an object or anatomical feature improperly griped, grasped or positioned in the jaw assembly (e.g., too far in a proximal direction in the jaw assembly, beyond the gripping portion, the electrically conductive portion, or a combination thereof) may not be properly coagulated. Advancing a cut blade onto a vessel or tissue that is not sufficiently grasped or coagulated, may undesirably cause bleeding or other trauma to the object or anatomical feature. Accordingly, the stabilizing tongue may function as a stop or alignment feature so that the object, vessel or tissue can be properly grasped and/or positioned between the jaws, relative to the gripping portions, the electrically conductive portions, or a combination thereof.

The one or more stabilizing tongues may be longer, shorter, or even the same size as than the one or more projections of the jaw shroud, stiffening spine, jaws, or a combination thereof. When the jaw assembly is in the open position, the one or more stabilizing tongues may extend towards and overhang or extend past an opposing jaw or jaw shroud. Accordingly, as an object or anatomical feature being located or placed between the jaws, the stabilizing tongue can act as a stop so that the object or anatomical feature is not placed too far back proximally into the jaw assembly.

The one or more stabilizing tongues may be free from contacting the gripping portion of an opposing jaw. Instead, preferably, the stabilizing tongue can be slipped, into or slide along, a side of an opposing jaw, jaw element, and/or jaw shroud when the jaw assembly is moved into a closed position. Preferably, the one or more jaw shrouds, stiffening spines, or both include one or more cavities or recesses. The one or more cavities or recesses are preferably aligned with a stabilizing tongue located on an opposing jaw shroud. The one or more cavities or recesses may therefore function to receive a stabilizing tongue of an opposing jaw shroud when the jaw assembly is in an open position and/or closed position.

The one or more stabilizing tongues may be located on one or both lateral sides of the jaw assembly. Preferably, each jaw shroud includes one stabilizing tongue. Preferably, the same jaw shroud can be attached to the top or bottom jaw and still function properly. Accordingly, when the jaw assembly includes two jaw shrouds, a stabilizing tongue is provided on each side of the jaw assembly.

The instrument may include one or more cut blades. The cut blade may function to cut an object or anatomical feature of interest, such as a vessel or tissue, for example. The cut blade may be a cutting blade, scalpel, etc. The cut blade can be located between the jaws, the jaw assembly, or both. The cut blade may be reciprocated within a cut blade channel or groove located in one or both of the jaws, gripping sections, gripping portions, or a combination thereof. In a neutral or steady state, the blade can be retracted. In a cut state, the blade can be moved or extended to cut an object, vessel or tissue captured between the jaw assembly (e.g., when the jaw assembly is in a closed or clamping position). The blade may be connected or affixed to one or more blade pushrods. The blade pushrods may also be connected to affixed to the hand piece or one or more mechanisms in the hand piece. The cut blade can be rotated about an axis. The cut blade can be rotated about an axis may be the same as the tubular member axis along which the tubular member is moved. Rotating the blade may provide for as user to advantageously alter an orientation of the approach of the blade to tissue without having, to twist the hand piece into a difficult or uncomfortable position, for example.

Figure 1:
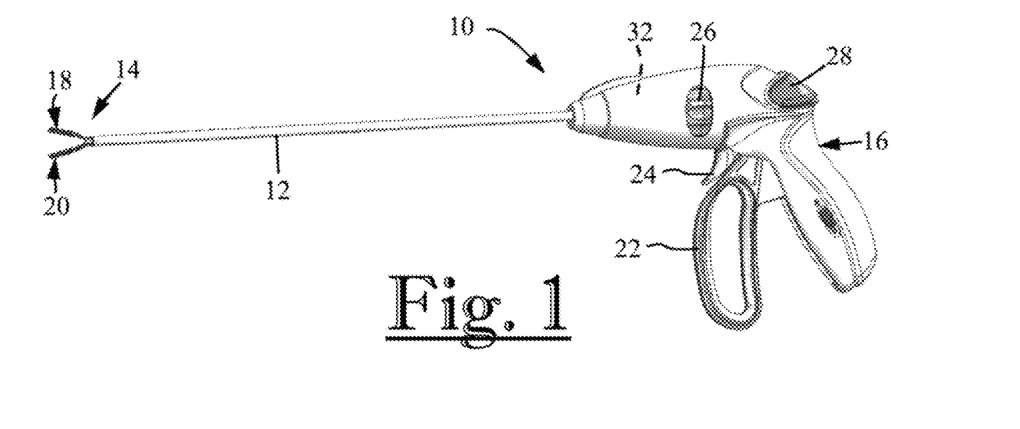
FIG. 1 is a perspective view of an instrument.

FIG. 1 illustrates the instrument 10. The instrument 10 includes a tubular member 12, as jaw assembly 14, and as hand piece 16. The jaw assembly 14 comprises as first jaw element 18 and a second jaw element 20. The hand piece 16 includes one or more user inputs or controls, including a lever 22, a trigger 24, a wheel 26, and a button 28.

Figure 2:
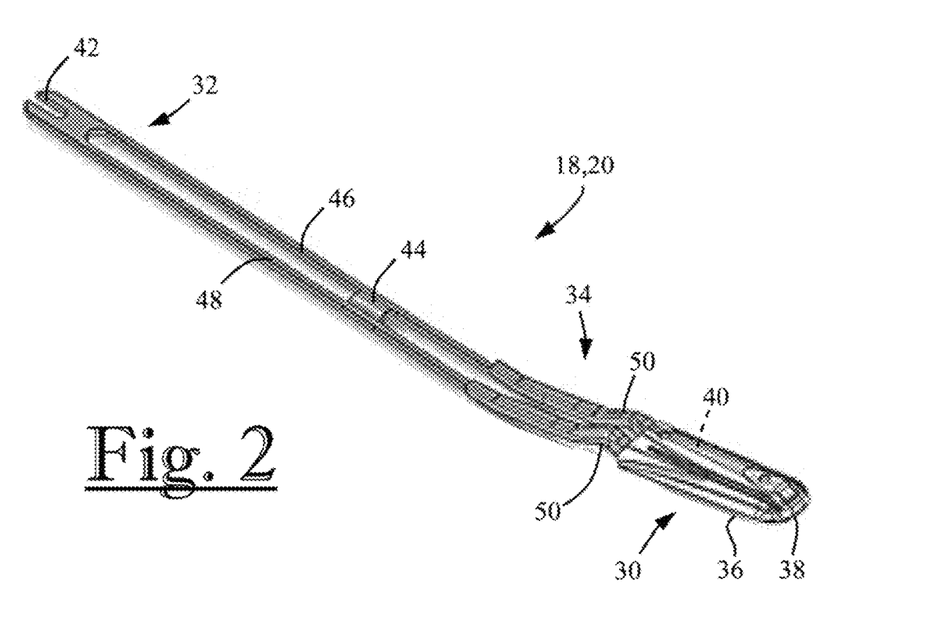
FIG. 2 is a perspective view of a jaw element of the instrument.

FIG. 2 illustrates an exemplary first jaw element 18, which may also be the second jaw element 20. The jaw element 18, 20 includes a gripping section 30, an anchoring section 32, and a flexing section 34. The gripping section 30 includes as jaw 36, as jaw shroud 38, and a stiffening spine 40. The anchoring section 32 includes a recess 42. The anchoring section 32 also includes a web 44 connecting a first anchoring section 46 to a second anchoring section 48. The flexing section 34 includes one or more arcuate sections 50.

Figure 3:
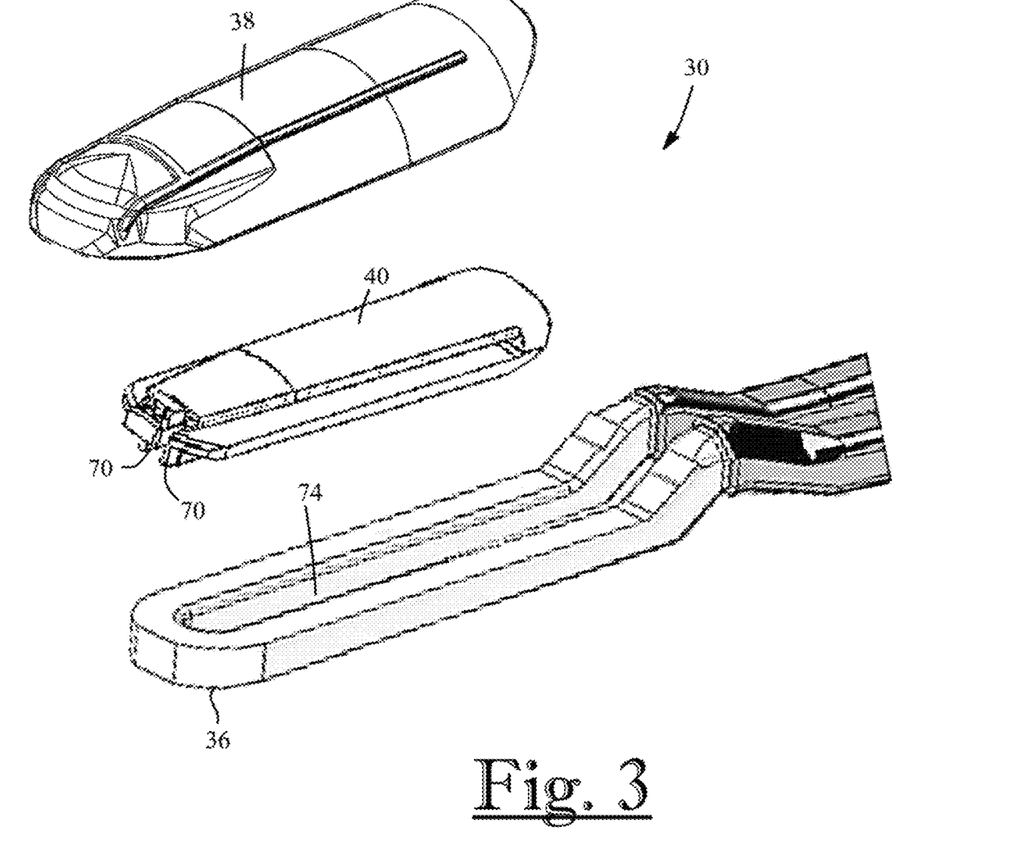
FIG. 3 is an exploded perspective view of a portion of the jaw element, a stiffening spine, and a jaw shroud.

FIG. 3 illustrates the gripping section 30 of the jaw element 18, 20 (FIG. 2). The gripping section includes a jaw 36, a jaw shroud 38, and a stiffening spine 40. The jaw 36 includes a channel 74 into which one or more projections 70 of the stiffening spine 40 may be received to attach the stiffening spine 40 to the jaw 36.

Figure 4:
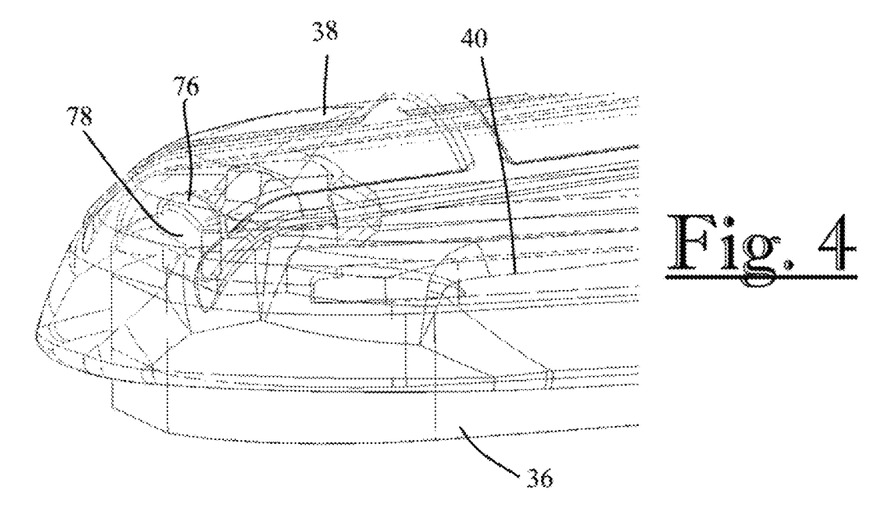
FIG. 4 is a perspective view of a portion of the jaw element, the stiffening spine, and the jaw shroud; the jaw shroud is shown in transparent.

FIG. 4 illustrates a portion of the gripping section 30, which includes a jaw 36, a jaw shroud 38, and a stiffening spine 40. The jaw shroud 36 includes a connecting feature 76 and the stiffening spine 40 includes an undercut feature 78. The connecting feature 76 and the undercut feature 78 may cooperate to attach the jaw shroud 36 to the stiffening spine 40 and therefore to the jaw 36.

Figure 5:
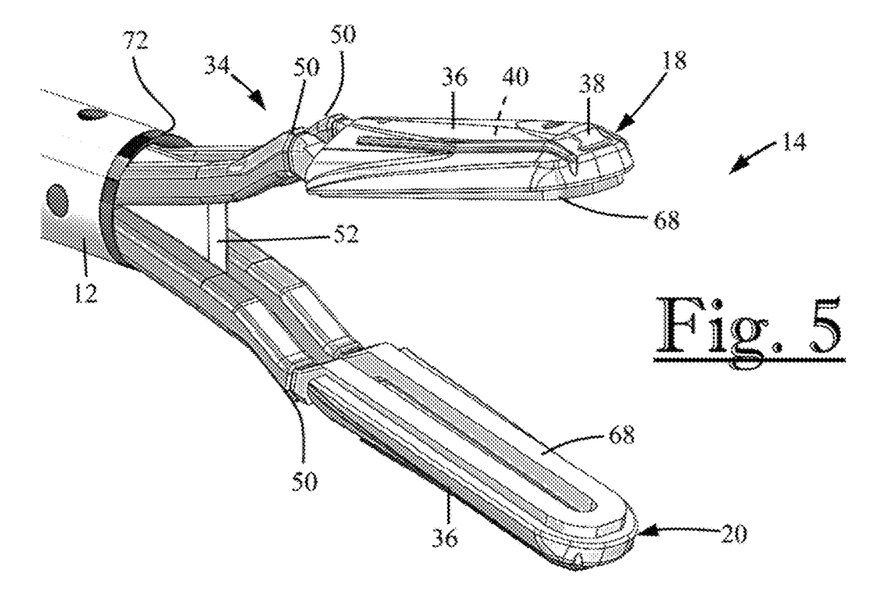
FIG. 5 is a perspective view of a portion of the jaw assembly including a cutting blade.

FIG. 5 illustrates the jaw assembly 14, which includes a first jaw element 18 and a second jaw element 20. The jaw assembly 14 is shown in an open position. The tubular member 12 includes a mouth or distal opening 72. The flexing sections 34 include arcuate sections 50. Moving the tubular member 12 distally into contact with or onto the arcuate sections 50 causes the jaw assembly 14 to move or flex from the open position to the closed position (See FIGS. 7c and/or 8b). A cut blade 52 is located between the jaw elements 18, 20. One or both of the jaws 36 includes a jaw shroud 38, a stiffening spine 40, and an electrode 68.

Figure 6:
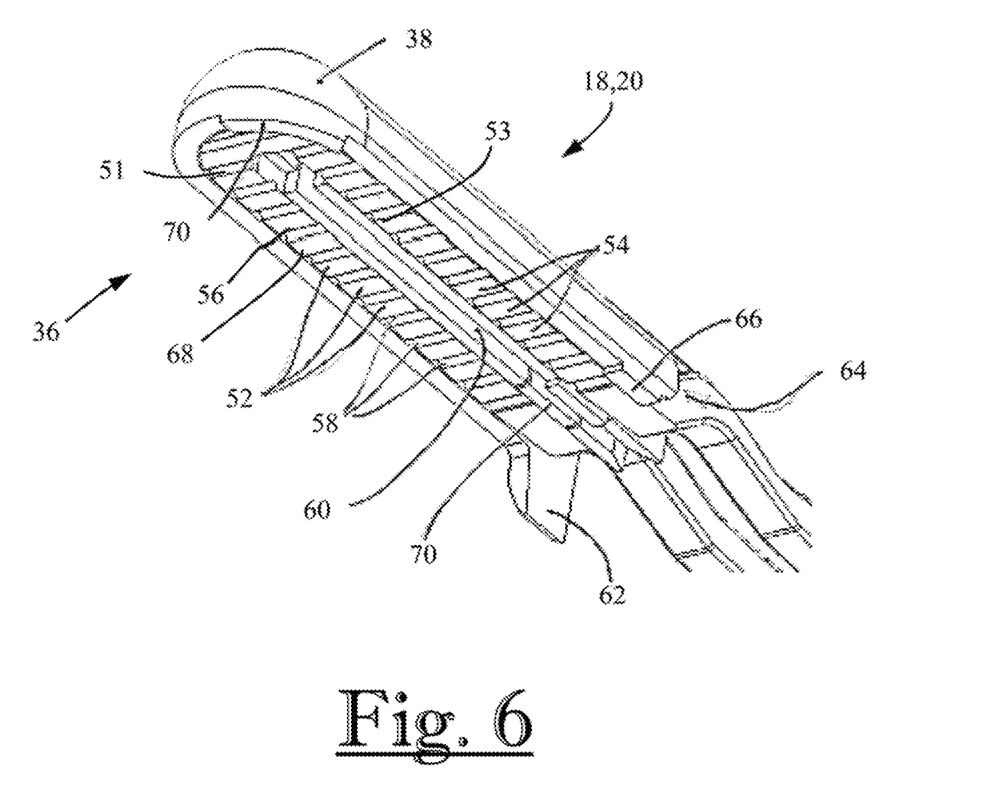
FIG. 6 is a partial perspective view of a jaw element.

FIG. 6 illustrates a portion of the jaw element 18, 20. The jaw 36 includes a gripping portion 51 and an electrically conductive portion 53. The jaw 36, the gripping portion 51, and/or the electrically conductive portion 53 includes teeth 52 and one or more electrodes 68. The teeth 52 can have flattened tops 54, sharp points 56, or both. Between teeth 52, the jaw 36 includes a trough 58. The jaw 36 also includes a cut blade slot 60 for the cut blade 52 (FIG. 5) to be moved or stored within. The jaw shroud 38 or the stiffening spine 40 includes a stabilizing tongue 62; a cavity or recess 64 for receiving a stabilizing tongue 62 located on an opposing jaw 36 (not illustrated); and a projection 66. The stiffening spine 40 also includes projections 70.

Figure 7A:
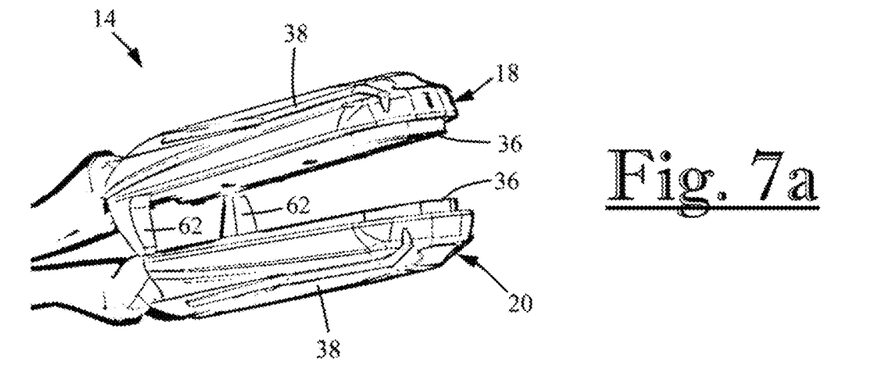
FIG. 7a is a side perspective view of a jaw assembly in an open position.
Figure 7B:
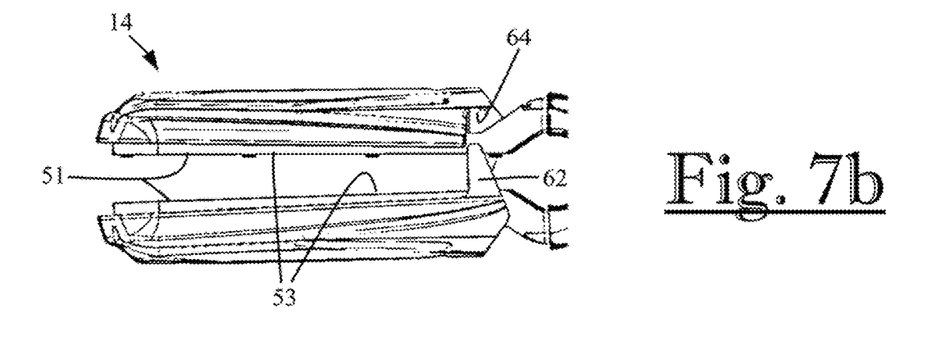
FIG. 7b is a side view of a jaw assembly in the open position.
Figure 7C:
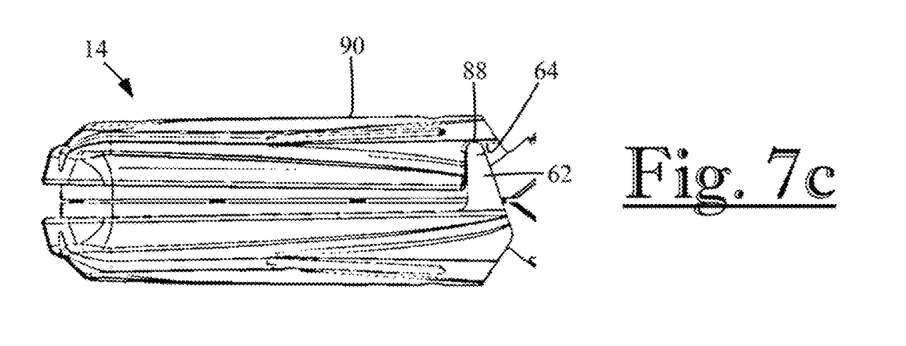
FIG. 7c is a side view of a jaw assembly in the closed position.

FIGS. 7a and 7b show a jaw assembly 14. Specifically, FIG. 7a shows the jaw assembly 14 in an open position, and FIG. 7b shows the jaw assembly 14 in the closed position. The jaw assembly 14 includes an opposing first and second jaw element 18, 20. Each of the jaw elements 18, 20 include a jaw 36 having a gripping portion 51 and an electrically conductive portion 53. The jaw shroud 38 or the stiffening spine 40 (not shown) includes a stabilizing tongue 62 and a cavity or recess 64 for receiving a stabilizing tongue 62 located on an opposing jaw shroud 38 or the stiffening spine 40. In the open position (FIG. 7b), the stabilizing tongue 62 can prevent an object or anatomical feature from being inserted or pushed too far proximally (i.e., towards the hand piece, for example). In the closed position (FIG. 7c), a tip 88 of the stabilizing tongue 64 is positioned below an outer or top surface 90 of jaw 18; that is, the tip 88 does not extend beyond the outer or top surface 90 of jaw 18 when the jaw is in the closed position and also the open position.

Figure 8A:
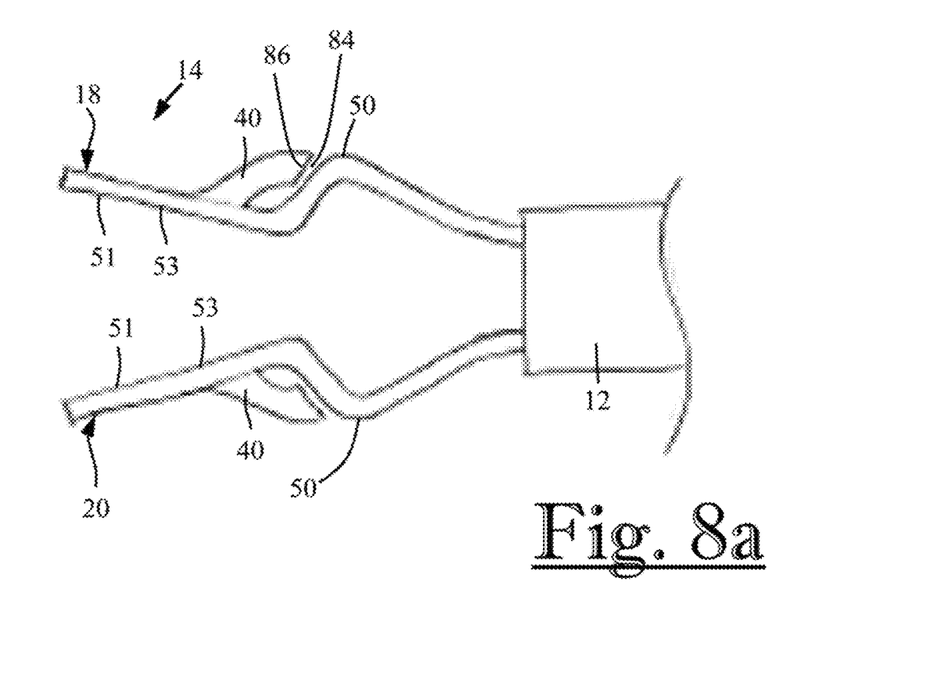
FIG. 8a is a side view of a jaw assembly in an open position.
Figure 8B:
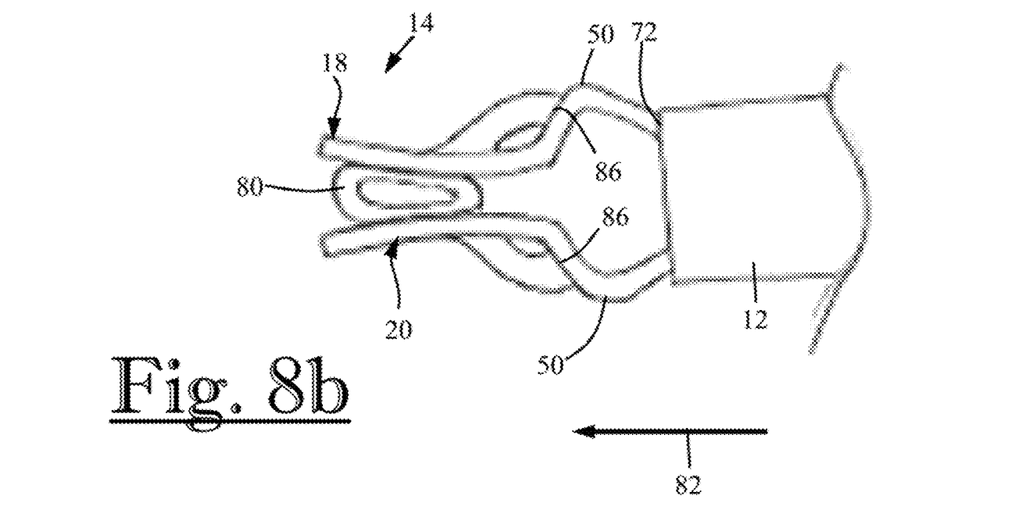
FIG. 8b is a side view of a jaw assembly in a closed position.

FIGS. 8a and 8b show a jaw assembly 14 and tubular member 12. FIG. 8a shows the jaw assembly 14 in an open position, and FIG. 8b shows the jaw assembly 14 in a closed portion with an object, vessel, or tissue 80 located between the jaws. The jaw assembly 14 includes a first jaw element 18 and to second jaw element 20. The first and second jaw elements 18 include stiffening spines 40 and arcuate sections 50. In the open position, a gap 84 is located between an edge 86 of the stiffening spine 40 and the arcuate portion 50 of the jaw elements 18, 20. During use, the tubular member 12 can be moved in a distal direction 82 so that the mouth 72 of the tubular member 12 contacts and/or moves over one or both of the arcuate sections 50. Further movement of the tubular member 12 in the distal direction 82 causes the gripping portions 51, the electrically conductive portion 53, or both oldie jaw elements 18, 20 to move or flex towards one another. Thereafter, the edges 84 of one or more of the stiffening spines 40 contact a portion of the arcuate section 50 of a corresponding jaw element 18, 20 so that the corresponding gaps 86 are taken up. Accordingly, the jaw elements 18, 20, the gripping portions 51, the jaws, or a combination thereof can be restricted or prevented from bending, flexing, or deflecting. Accordingly, a substantially uniform grasping or gripping pressure can be provided along an entire length of the gripping portions 51.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission M the following claims of any aspect of subject matter that is disclosed herein is not a disclaimer of such subject matter, nor should it be regarded that the inventors did not consider such subject matter to be part of the disclosed inventive subject matter.

The invention claimed is:

1. An instrument comprising:
a forceps comprising:
   i. a hand piece;
   ii. a tubular member connected to the hand piece; and
   iii. a jaw assembly connected to the hand piece, the jaw assembly comprising:
      a. a first jaw element comprising a gripping section and a flexing section, the flexing section includes an arcuate section;
      b. a second jaw element opposing the first jaw element, the second jaw element comprises a gripping section;
   wherein the tubular member is moveable onto the arcuate section of the first jaw element so that the flexing section of the first jaw element is flexed and the jaw assembly is moved into a closed position,
   wherein the first jaw element, the second jaw element, or both includes a stiffening spine so that the jaw assembly is substantially rigid in the closed position,
   wherein the first jaw element is electrically conductive, and the second jaw element is electrically conductive, and the first jaw element, the second jaw element, or both includes an electrically insulating jaw shroud, and
   wherein the stiffening spine secures the jaw shroud to the first jaw element, the second jaw element, or both.

2. The instrument of claim 1, wherein the second jaw element comprises a flexing section including an arcuate section, and
   wherein the tubular member is moveable onto the arcuate section of the first jaw element and onto the arcuate section of second jaw element so that the flexing section of the first jaw element is flexed and the flexing section of the second jaw element is flexed and the jaw assembly is moved into the closed position.

3. The instrument of claim 1, wherein the jaw shroud includes a connecting feature and the stiffening spine includes an undercut feature, and
   wherein the connecting feature and the undercut feature are connected together.

4. The instrument of claim 1, wherein the jaw shroud includes one or more projections so that in the closed position, the one or more projections provide a stand off so that the gripping section of the first jaw element and the gripping section of the second jaw element are prevented from touching.

5. The instrument of claim 4, wherein the gripping section of the first jaw element, the gripping section of the second jaw element, or both includes an electrode.

6. The instrument of claim 1, wherein the stiffening spine includes one or more projections so that in the closed position, the one or more projections provide a stand off so that the gripping section of the first jaw element and gripping section of the second jaw element are prevented from touching.

7. The instrument of claim 1, wherein the jaw shroud includes a stabilizing tongue that provides lateral stability to the jaw assembly when the jaw assembly is in the closed position or when the jaw assembly is moved into the closed position.

8. The instrument of claim 1, wherein the jaw shroud includes a stabilizing tongue extending from a proximal end of the jaw shroud so that an object is prevented from extending beyond a proximal end of one or more electrically conductive surfaces relative to the hand piece.

9. The instrument of claim 1, wherein the jaw assembly is free of any pivoting joints or mechanisms.

10. The instrument of claim 1, wherein a proximal end of the flexing section of the first jaw element is restricted from moving distally, proximally, or both relative to the hand piece.

11. The instrument of claim 1, wherein the gripping section of the first jaw element, the gripping section of the second jaw element, or both includes a cutting blade slot for reciprocating a cutting blade.

12. An instrument comprising:
a forceps comprising:
   i. a hand piece;
   ii. a tubular member moveably connected to the hand piece; and
   iii. a jaw assembly connected to the hand piece, the jaw assembly comprising:
      a. a first jaw element comprising a gripping portion, a flexing section, and an arcuate section;
      b. a second jaw element comprising a gripping portion and an arcuate section;
   wherein the tubular member is moveable onto the arcuate section of the first jaw element and onto the arcuate section of the second jaw element so that the flexing section of the first jaw element is flexed and the arcuate section of the second jaw element is flexed and the jaw assembly is moved into a closed position,
   wherein the first jaw element includes a jaw shroud so that a uniform gripping pressure is provided along the gripping portion of the first jaw element and the gripping portion of the second jaw element, and
   wherein the first jaw element, the second jaw element, or both includes a stiffening spine so that the gripping portion of the first jaw element, the gripping portion of the second jaw element, or both is prevented from deflecting when the jaw assembly is in the closed position.

13. The instrument of claim 12, wherein the stiffening spine secures the jaw shroud to the first jaw element, the second jaw element, or both.

14. An instrument comprising:
a forceps comprising:
   i. a hand piece;
   ii. a tubular member moveably connected to the hand piece; and
   iii. a jaw assembly connected to the hand piece, the jaw assembly comprising:
      a. a first jaw element comprising a gripping portion and an arcuate section;
      b. a second jaw element comprising a gripping portion and an arcuate section;
      iv. a stabilizing spine connected to one or both of the first jaw element and the second jaw element; and
      v. a jaw shroud connected to the stabilizing spine;
   wherein the tubular member is moveable over the arcuate section of the first jaw element and the arcuate section of the second jaw element so that both the first jaw element and the second jaw element are flexed and the jaw assembly is moved into a closed position, and
   wherein the stabilizing spine and the jaw shroud restrict the gripping portion of the first jaw element, the gripping portion of the second jaw element, or both from deflecting when the jaw assembly is in the closed position so that a uniform gripping pressure is provided along the gripping portion of the first jaw element and the gripping portion of the second jaw element.

15. The instrument of claim 14, wherein the jaw shroud includes a stabilizing tongue extending near a proximal end of the jaw shroud so that an object is prevented from extending beyond a proximal end of the gripping portion relative to the hand piece.

16. A method of using the instrument of claim 12, comprising:
arranging an object between the gripping portion of the first jaw element and the gripping portion of the second jaw element;
moving the tubular member over the arcuate section of the first jaw element and the arcuate section of the second jaw element so that both the first jaw element and the second jaw element are flexed and the jaw assembly is moved into the closed position;
moving the tubular member off of the arcuate section of the first jaw element and the arcuate section of the second jaw element so that both the first jaw element and the second jaw element are relaxed and the jaw assembly is moved into an open position; and
wherein in the open position, the gripping portion of the first jaw element is in a spaced apart relationship relative to the gripping portion of the second jaw element.

17. The method of claim 16, wherein the method includes performing one or more functions on the object, the one or more functions including:
capturing the object;
grasping the object;
providing a clamping force to secure the object;
retracting the object; and/or
providing a compression force across the object.

18. The method of claim 16, wherein the method includes a step of:
rotating the jaw assembly, a cutting blade, or both relative to the hand piece, and
wherein the jaw assembly is restricted from moving distally, proximally, or both relative to the hand piece.

19. The method of claim 16, wherein the jaw shroud includes a stabilizing tongue, and
wherein in the closed position, the stabilizing tongue is prevented from contacting the gripping portion of the first jaw element, the gripping portion of the second jaw element, or both.

20. The method of claim 16, wherein the jaw assembly includes one or more projections so that in the closed position, the one or more projections provide a stand off so that the gripping portion of the first jaw element is prevented from contacting the gripping portion of the second jaw element.

21. An instrument comprising:
a forceps comprising:
 i. a hand piece;
 ii. a tubular member connected to the hand piece; and
 iii. a jaw assembly connected to the hand piece, the jaw assembly comprising:
  a. a first jaw element comprising a gripping section and a flexing section, the flexing section includes an arcuate section;
  b. a second jaw element opposing the first jaw element, the second jaw element comprises a gripping section;
wherein the tubular member is moveable onto the arcuate section of the first jaw element so that the flexing section of the first jaw element is flexed and the jaw assembly is moved into a closed position,
wherein the first jaw element, the second jaw element, or both includes a stiffening spine so that the jaw assembly is substantially rigid in the closed position, and
wherein the stiffening spine includes one or more projections so that in the closed position, the one or more projections provide a stand off so that the gripping section of the first jaw element and the gripping section of the second jaw element are prevented from touching.

* * * * *

UNITED STATES PATENT AND TRADEMARK OFFICE
CERTIFICATE OF CORRECTION

PATENT NO. : 10,456,154 B2  
APPLICATION NO. : 15/386537  
DATED : October 29, 2019  
INVENTOR(S) : Murdeshwar et al.

Page 1 of 1

It is certified that error appears in the above-identified patent and that said Letters Patent is hereby corrected as shown below:

On the Title Page

In item (71), in "Applicant", in Column 1, Line 1, after "INC.,", insert --d/b/a Olympus Surgical Technologies America--

In item (73), in "Assignee", in Column 1, Line 1, after "INC.,", insert --D/B/A OLYMPUS SURGICAL TECHNOLOGIES AMERICA--

In the Claims

In Column 17, Line 53, in Claim 6, after "and", insert --the--

Signed and Sealed this  
Second Day of March, 2021

Drew Hirshfeld  
*Performing the Functions and Duties of the*  
*Under Secretary of Commerce for Intellectual Property and*  
*Director of the United States Patent and Trademark Office*